United States Patent [19]

Becker

[11] Patent Number: 5,518,007
[45] Date of Patent: May 21, 1996

[54] ELECTRODE LOCATOR

[76] Inventor: Joseph H. Becker, 1504 Williamsburg, Plano, Tex. 75074

[21] Appl. No.: 347,695

[22] Filed: Dec. 1, 1994

[51] Int. Cl.⁶ .................................................. A61B 5/0476
[52] U.S. Cl. ........................ 128/774; 128/644; 128/731; 33/512
[58] Field of Search .................... 128/639, 644, 128/731, 774; 607/115, 139, 148, 149; 33/512

[56] References Cited

U.S. PATENT DOCUMENTS

| | | | |
|---|---|---|---|
| 2,426,958 | 9/1947 | Ulett, Jr. et al. | 128/644 |
| 3,998,213 | 12/1976 | Price | 128/644 |
| 4,035,739 | 4/1978 | Sams | 128/644 |
| 4,072,145 | 2/1978 | Silva | 128/644 |
| 4,709,702 | 12/1987 | Sherwin | 128/644 |
| 4,928,696 | 5/1990 | Henderson et al. | 128/644 |
| 4,967,038 | 10/1990 | Gevins et al. | 128/644 |
| 5,119,816 | 6/1992 | Gevins | 128/644 |
| 5,293,867 | 3/1994 | Oommen | 128/639 |
| 5,313,952 | 5/1994 | Hoch | 128/644 |

OTHER PUBLICATIONS

Blom et al, "An electrode cap tested", Electroencephalography and Clinical Neurophysiology, 54, 591–594, 1982.

*Primary Examiner*—Lee S. Cohen
*Attorney, Agent, or Firm*—Daniel V. Thompson

[57] ABSTRACT

A measurement device is provided in various lengths determined by head size. The measurement devices are manufactured from an agile, non-elastic material enclosing an open structure on the length of the device that coincides with an international system for placement of scalp electrodes.

5 Claims, 2 Drawing Sheets

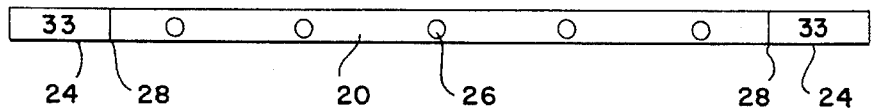
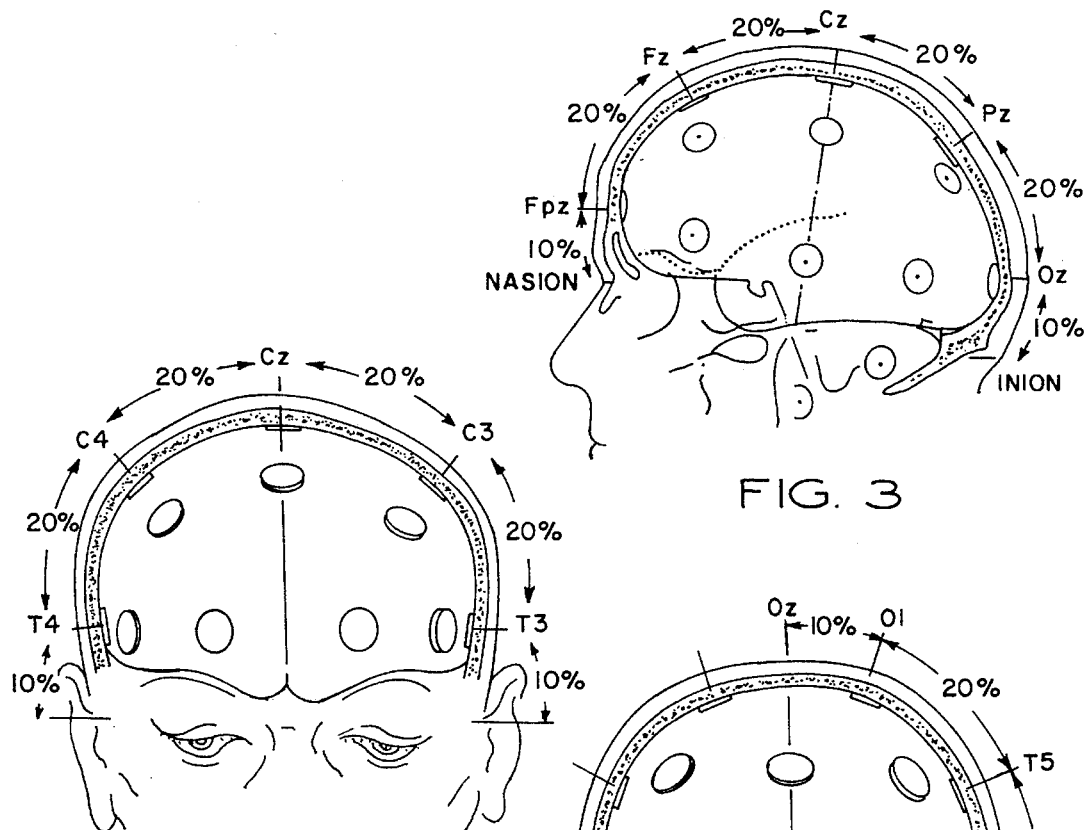
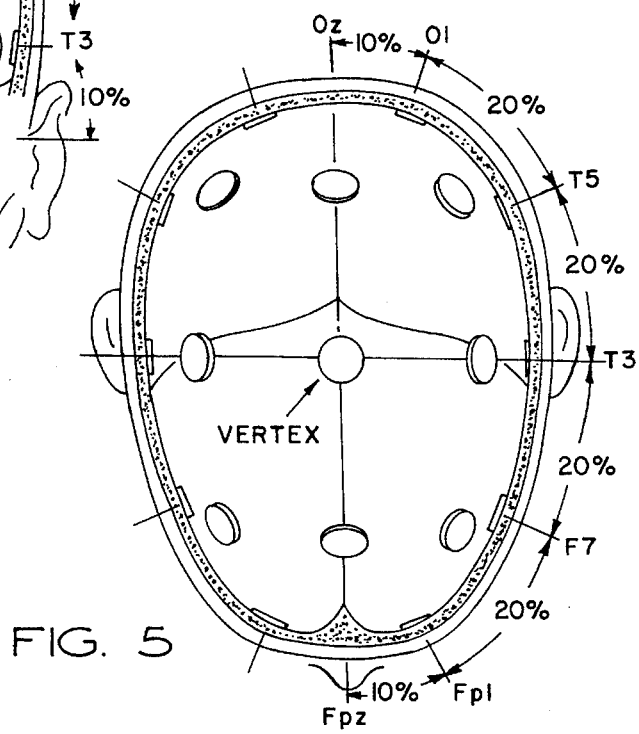

ELECTRODE LOCATOR

BACKGROUND

1. Field of Invention

This invention relates to the area of EEG (Electroencephalography) and the study of evoked brain potentials.

2. Description of Prior Art

A system to define a standard set of electrode placements on the scalp, so that results obtained in different clinics and laboratories could be compared, was devised by Herbert H. Jasper, M.D. and subsequently adopted for trial at the meeting in 1949 of the General Assembly of the International Federation in Paris. Dr. Jasper's scheme defines a set of electrode placements on the scalp whose relative position will be determined by the dimensions of each individual's head so that electrodes placed on heads of different dimensions will be in comparable locations on the scalp (Jasper, 1958). This system is based on a set of latitudinal and longitudinal arcs upon the surface of an approximately spherical cranium, and positions of electrodes are determined by measurements from standard landmarks (i.e., nasion, inion, and pre auricular points) on the skull. Arc length measurements from nasion to inion (FIG. 3) and from the pre-auricular point of one ear over vertex to the opposite ear (FIG. 4) are taken as well as a measurement around the circumference (FIG. 5). Electrodes are then placed at locations 10, 20, 20, 20, 20, and 10% along each of these arcs as shown in FIGS. 3, 4, and 5 respectively. Thus, the name of this system has been designated as "the 10/20 international system".

Heretofore, the placement of electrodes on the scalp according to the International 10–20 system has been ascertained by mainly one of two methods: (1) the laboratory technician measures each arc length with a flexible tape (such as one used by a seamstress or tailor), then calculates the appropriate 10 and 20 percentages (often the 20% interval is set using a pair of blunt tipped calipers) to locate the appropriate sites for electrodes that are subsequently affixed on the scalp; (2) Electrode caps are employed to record the electrical activity from the scalp.

An electrode cap (U.S. Pat. No. 4,025,739) was described by Mr. Marvin Sams April 1978, and subsequently another by Mr. Gary W. Sherwin (U.S. Pat. No. 4,709,702) Dec. 1985. Presently electrode caps of various sizes, according to the 10/20 system, have been designed and are marketed by Electro-Cap International, Inc. in Eaton, Ohio (FIG. 1) and perhaps others; however, a simple tool, such as the "electrode locator" that will complement basic measurement procedures and reduce electrode application time has not been devised and introduced to the scientific community. Electrode cap systems accommodate various head sizes, but to do so can require as many as seven different caps; and still there remains head circumferences outside the range of standard caps. The cost of this system is an important factor to be considered. In many instances, especially in research studies, a limited number of specified electrode sites are assessed and a cap is not a consideration. The cap cannot be used in clinical applications where skull defects are present, in situations where pressure on the skull is detrimental, or on severely injured patients that cannot be fixed with straps (Blom and Anneveldt, 1982). Many users, therefore, would find it desirable to have a simple tool that could facilitate the electrode placement on the scalp at relatively low cost.

OBJECTS AND ADVANTAGES

Accordingly I claim the following as objects and advantages of the invention: to provide a tool for easily, neatly, and reliably locating the placement of electrodes on the scalp according to the 10/20 international system for the recording of brain electrical activity, regardless of the size or configuration of the head; and to provide such a tool that requires a minimum of skill and training to use.

Readers will find further objects and advantages of the invention from a consideration of the ensuing description and the accompanying drawings.

DRAWINGS FIGURES

FIG. 2 shows a top view of the "electrode locator", according to the invention, that is used to index the location of the electrode placements; for example, between the nasion and inion of a head (FIG. 3) that measures 33 centimeters.

FIG. 3 shows a perspective side view of a head illustrating the nasion to inion arc measure with appropriate percentages aligned according to the 10/20 international system.

Figure 1:
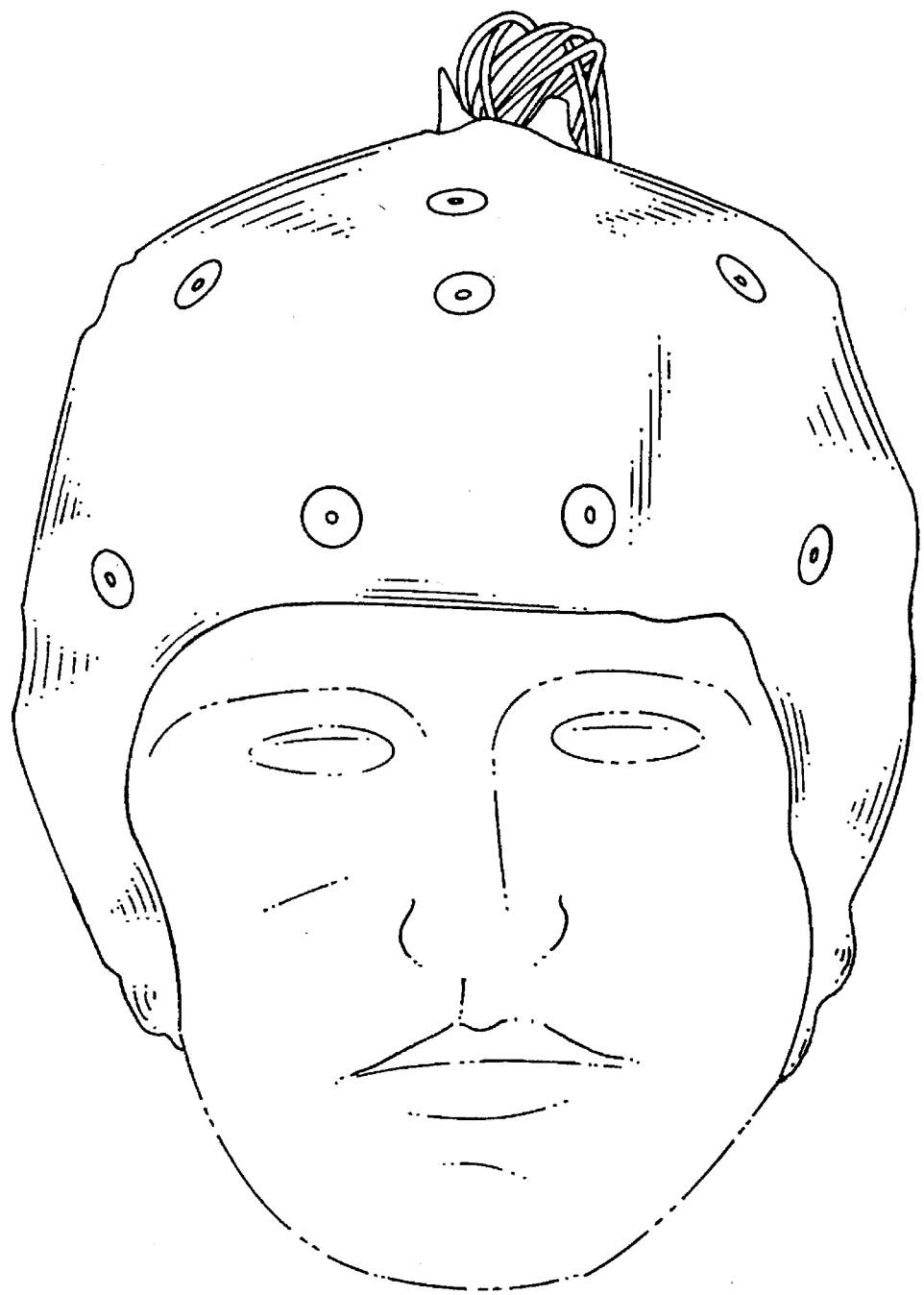
FIG. 1 is an illustration of Prior Art apparatus.

The "electrode locator" of FIG. 2 is also used to index the location of the electrode placements between the two ears of a head (FIG. 4) that, for example, measures 33 centimeters.

FIG. 4 shows a perspective front view of a head illustrating the central line measurement from one ear to the other with appropriate percentages aligned according to the 10/20 international system.

An "electrode locator", similar but perhaps smaller (i.e., 27 centimeters) than that of FIG. 2 is also used to index electrode placements around either side of the circumference of the head.

FIG. 5 shows the top perspective view of the head illustrating the measures, taken around the circumference of the scalp, from a location labeled Fpz in the front to a site in the posterior labeled Oz. The two sides of the head are usually symmetrical, so the same locator is used to index both sides. FIG. 5 illustrates how only one-half of the head is used for the particular electrode locator.

DRAWING REFERENCE NUMERALS

Agile and non elastic material.

Measure of arc distance (i.e., distance between nasion and inion (FIG. 3), pre-auricular points (FIG. 4), and one-half of the head circumference [Fpz to Oz] as in FIG. 5). This measure is used to categorize the electrode locator.

Measure used to categorize the electrode locator strip.

Open structure or hole in material of locator strip to be used as index for location for electrode placement.

Position or index for nasion/inion (FIG. 3), pre-auricular points FIG. 4), and Oz/Fpz (FIG. 5) on the locator strip.

ELECTRODE LOCATOR—DESCRIPTION

FIG. 2 shows a single-piece "electrode locator" according to the preferred embodiment of the invention. The "electrode locator" comprises a length of agile, but non-elastic, material enclosing open structures, or holes, at appropriate 10 and 20 percent positions in accordance with a specific arc measurement of the head that coincide with the 10/20 international system for placement of electrodes. "Electrode locators" are categorized according to the dimension of length, in centimeters, that correspond to the arc measurements of the head. The interval of measure separating the various locators is one centimeter. This tool can be used by those interested in EEG and other brain electrical activity measurements from the scalp. In the preferred embodiment, the electrode locator is manufactured from a material considered to be disposable in practice. The electrode locators are preferably supplied on a roll containing multiple electrode locators and perforated (or otherwise slit) to cause easy separation at the required lengths.

ELECTRODE LOCATOR—OPERATION

Utilizing standard landmarks (i.e., the nasion, inion, and pre-auricular sites), the head is first measured with a tape to obtain arc length measurements in centimeters between nasion and inion, preauricular points, and from Fpz to Oz (FIGS. 3, 4, and 5 respectively). After establishing the arc length, the "electrode locator" corresponding to that measure of length is used to determine the location of specific electrode placements. The appropriate "electrode locator" is extended between the two points where the measurements were initially taken with the tape measure.

Using the open structures, or holes, of the "electrode locator" as an index, a mark (i.e., with a grease pencil) is made on the scalp for the location of the electrode placement. After the location for the electrodes have been established and marked, the scalp can then be prepared and the electrode placed according to normal practice.

I claim:

1. A measurement system, comprising a plurality of electrode locators of various lengths, said electrode locators formed of agile non-elastic material enclosing a plurality of open structures along said lengths that coincide with an international system for placement of scalp electrodes.

2. The system of claim 1 wherein said international system for placement of electrodes is the 10/20 international system for placement of electrodes.

3. The system of claim 1 wherein said open structures are comprised of eyelets appropriately inserted into said material along its lengths.

4. The system of claim 1 wherein a length dimension is indicated on an extremity of each electrode location.

5. The system of claim 1 wherein said material is disposable.

* * * * *

UNITED STATES PATENT AND TRADEMARK OFFICE
CERTIFICATE OF CORRECTION

PATENT NO. : 5,518,007
DATED      : May 21, 1996
INVENTOR(S): Joseph H. Becker

It is certified that error appears in the above-indentified patent and that said Letters Patent is hereby corrected as shown below:

```
Col. 2, line 43, insert -- 20 -- Before "Agile".
Col. 2, line 44, insert -- 22 -- Before "Measure".
Col. 2, line 48, insert -- 24 -- Before "Measure".
Col. 2, line 49, insert -- 26 -- Before "Open".
Col. 2, line 51, insert -- 28 -- Before "Position".
```

Signed and Sealed this

Twentieth Day of August, 1996

Attest:

BRUCE LEHMAN

*Attesting Officer*   *Commissioner of Patents and Trademarks*